United States Patent
Brill

(10) Patent No.: US 10,048,595 B2
(45) Date of Patent: Aug. 14, 2018

(54) PROCESS CONTROL USING NON-ZERO ORDER DIFFRACTION

(71) Applicant: NOVA MEASURING INSTRUMENTS LTD., Rehovot (IL)

(72) Inventor: Boaz Brill, Rehovot (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 15/430,568

(22) Filed: Feb. 13, 2017

(65) Prior Publication Data

US 2017/0205716 A1 Jul. 20, 2017

Related U.S. Application Data

(63) Continuation of application No. 13/978,720, filed as application No. PCT/IB2012/050157 on Jan. 12, 2012, now Pat. No. 9,568,872.

(60) Provisional application No. 61/431,866, filed on Jan. 12, 2011.

(51) Int. Cl.
| | |
|---|---|
| *G01B 11/04* | (2006.01) |
| *G03B 27/32* | (2006.01) |
| *G03B 27/74* | (2006.01) |
| *G03F 7/20* | (2006.01) |
| *G01N 21/47* | (2006.01) |

(52) U.S. Cl.
CPC ..... *G03F 7/70516* (2013.01); *G01N 21/4788* (2013.01)

(58) Field of Classification Search
CPC .......... G01B 2210/56; G01N 21/4788; G01N 2021/8416; G03F 7/705; G03F 7/70616; G03F 7/70625; G03F 7/70633; G03F 7/70641; G03F 7/70683; G03G 15/50; H01L 22/12; H01L 2924/0002
USPC ................. 355/67, 68, 77; 356/636; 430/30
See application file for complete search history.

(56) References Cited

U.S. PATENT DOCUMENTS

2007/0105029 A1* 5/2007 Ausschnitt .......... B81C 99/0065
430/30

* cited by examiner

*Primary Examiner* — Colin Kreutzer
(74) *Attorney, Agent, or Firm* — Alphapatent Associates, Ltd; Daniel J. Swirsky

(57) ABSTRACT

A method of controlling a manufacturing process, the method including the steps of a) providing a testing area with a periodic structure, where the periodic structure includes a series of sets of patterned features, b) illuminating the periodic structure with a light, thereby producing a non-zero order diffraction signal, c) collecting the diffraction signal to produce a test signature, d) matching the test signature with a reference signature, where the reference signature was previously produced by performing steps a), b), and c) with respect to a reference structure that is at least similar to the periodic structure, and e) controlling a manufacturing process using a control setting set associated with the matching reference signature.

13 Claims, 15 Drawing Sheets

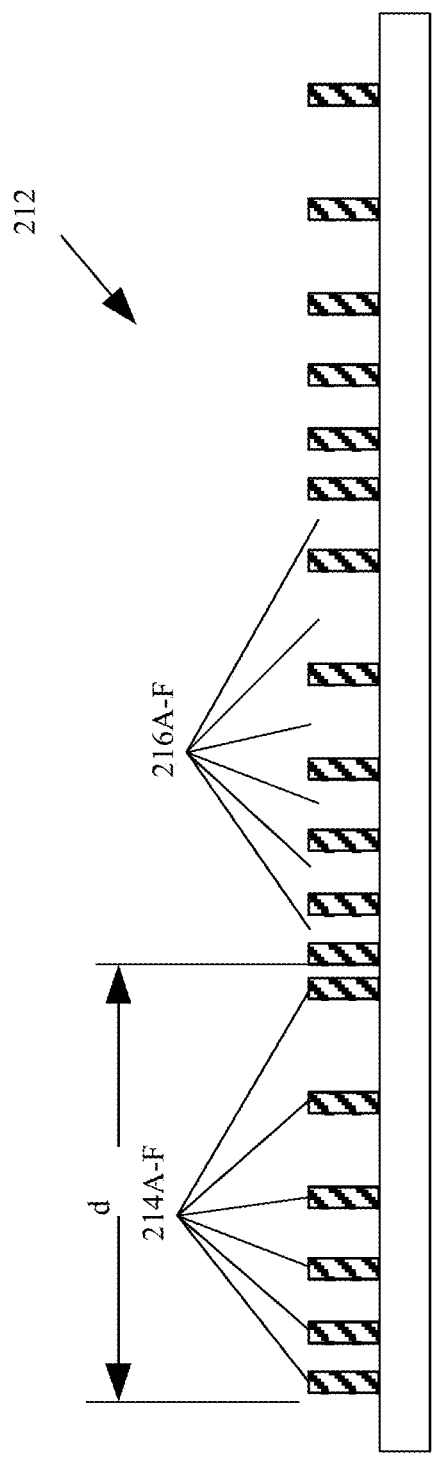

PROCESS CONTROL USING NON-ZERO ORDER DIFFRACTION

CROSS-REFERENCE TO RELATED APPLICATIONS

This application is a continuation of U.S. patent application Ser. No. 13/978,720 which is a U.S. National Phase Application under 35 U.S.C. 371 of International Application No. PCT/IB2012/050157, which has an international filing date of Jan. 12, 2012, and which claims the benefit of priority from U.S. Provisional Patent Application No. 61/431,866, filed on Jan. 12, 2011, which applications are incorporated herein by reference in their entirety.

FIELD OF THE INVENTION

This invention is generally in the field of process control techniques, and relates to a method and system for controlling a process of manufacturing patterned structures, such as photolithography and etching processes.

BACKGROUND OF THE INVENTION

Recently, tools based on scatterometry have been developed for process control in photolithography, and particularly for micro-lithography, which provide for high accuracy and repeatability, faster measurement, smaller volume and lower cost. Scatterometry is a method by which the signature, or optical response, of a periodic structure is measured. The signature may be obtained by measuring the optical properties of a structure, such as reflectance, ellipsometric or other parameters, as a function of one or more light parameters, such as the angle of incidence, polarization or wavelength. Thus, term "signature" may refer to an optical response of the structure to predetermined incident light. Due to the periodicity of the structure, it is possible to theoretically calculate the signature of a given sample using exact models thereof, such as in accordance with Rigorous Couple Wave Theory (RCWT), where a measured signature is correlated with theoretically calculated signatures that fit the structure's parameters. This fitting method suffers from such drawbacks as long calculation time, in-adequacy to real-time calculations, and the need for detailed knowledge about the structure, such as optical constants, that is required as input to the model. The problem of long calculation time is usually overcome by preparing a library of pre-calculated signatures. This procedure, however, requires a long setup time. The detailed knowledge about the structure, in many cases, also requires preliminary setup processes, such as material characterization. Yet another problem is the complicated, sometimes indirect relation between the process parameters, such as focus and exposure, and the profile parameters, where attempting to control the process by modifying process parameters based on profile information is difficult to implement. These problems impede the application of scatterometry-based systems as a production tool, specifically for integrated monitoring that require a fast feedback for process control. Additionally, since the accuracy of any measurement depends on the precision of the measuring device, any error of the measuring device decreases the reliability of such measuring techniques. Therefore, there is a need for an improved and efficient method for photolithographic process control.

SUMMARY OF THE INVENTION

In one aspect of the invention a method of controlling a manufacturing process is provided, the method including the steps of a) providing a testing area with a periodic structure, where the periodic structure includes a series of sets of patterned features, b) illuminating the periodic structure with a light, thereby producing a non-zero order diffraction signal, c) collecting the diffraction signal to produce a test signature, d) matching the test signature with a reference signature, where the reference signature was previously produced by performing steps a), b), and c) with respect to a reference structure that is at least similar to the periodic structure, and e) controlling a manufacturing process using a control setting set associated with the matching reference signature.

In another aspect of the invention the manufacturing process is a lithography process, and the control setting set includes any of exposure energy and focus conditions of expositing light.

In another aspect of the invention the periodic structure is present on a semi-conductor wafer.

In another aspect of the invention any of steps a), b), c), d) and e) are performed to control a lithography process applied to structures progressing on a production line.

In another aspect of the invention the method further includes selecting a wavelength of the light, where the non-zero order diffraction signal is produced when the light of the selected wavelength illuminates the periodic structure.

In another aspect of the invention the illuminating is performed at a first angle with respect to the periodic structure, the collecting is performed at a second angle with respect to the periodic structure, and the illuminating and the collecting are performed at different points in space.

In another aspect of the invention the reference signature and the test signature are obtained using at least similar periodic structures, illumination wavelengths, and manufacturing processes.

In another aspect of the invention the method further includes configuring each of the sets to have the same patterned features, and configuring each of the sets to have the same orientation in the series.

In another aspect of the invention the method further includes configuring each of the sets with asymmetrically patterned features, where the processing of the test signature includes determining a differential signature using a positive diffraction signal and a negative diffraction signal, and where both the positive diffraction signal and the negative diffraction signal are included in the non-zero order diffraction signal.

In another aspect of the invention the providing includes providing the periodic structure having a period d that is greater than a wavelength $\lambda$ of the light divided by two.

In another aspect of the invention the providing includes providing the periodic structure having a period d, where the illuminating includes selecting a wavelength $\lambda$ of the light, and where $\lambda \sim d$.

In another aspect of the invention the method further includes selecting a wavelength $\lambda$ of the light in a manner to produce the non-zero order diffraction signal when the light of wavelength $\lambda$ illuminates the periodic structure.

In another aspect of the invention the providing includes providing the periodic structure having a period d, where within each period d the periodic structure includes a plurality of alternating lines and spaces, and where the widths of the lines and the spaces vary randomly, thereby producing different intensities for diffraction orders +1 and −1 when the periodic structure is illuminated.

In another aspect of the invention the providing includes providing the periodic structure having a period d, where within each period d the periodic structure includes a plurality of alternating lines and spaces, and where the widths of lines and the spaces increase monotonically, thereby producing different intensities for diffraction orders +1 and −1 when the periodic structure is illuminated.

In another aspect of the invention the providing includes providing the periodic structure having a period d, where within each period d the periodic structure includes a plurality of alternating lines and spaces, where the width of the lines is constant, and where the width of the spaces increases monotonically, thereby producing different intensities for diffraction orders +1 and −1 when the periodic structure is illuminated.

In another aspect of the invention the providing includes providing the periodic structure where the sets are arranged in back-to-back pairs.

In another aspect of the invention the providing includes providing the periodic structure having a period d, where within each period d the periodic structure includes a plurality of identical sets of alternating lines and spaces, where the width of the lines is constant, and where the width of the spaces increases monotonically.

In another aspect of the invention the providing includes providing the periodic structure having a period d, where within each period d the periodic structure includes a plurality of identical sets of alternating lines and spaces, where the lines are identical to each other, where the thickness of each of the lines varies over its the length and increases monotonically to a midpoint of the line from both ends of the line, and where the width of the spaces increases monotonically.

In another aspect of the invention the providing includes providing the periodic structure having a period d, where within each period d the periodic structure includes a plurality of identical sets of alternating lines and spaces, where the size of the lines is uniform, where the lines are characterized by any of sharp edges, sharp corners, and being printed using non-printing assist features, and where the width of the spaces increases monotonically.

BRIEF DESCRIPTION OF THE DRAWINGS

The invention will be understood and appreciated more fully from the following detailed description taken in conjunction with the appended drawings in which:

FIGS. 2A-G are simplified conceptual illustrations of periodic structures useful with a non-zero order diffraction technique, constructed and operative in accordance with an embodiment of the invention.

DETAILED DESCRIPTION OF THE INVENTION

Figure 1A:
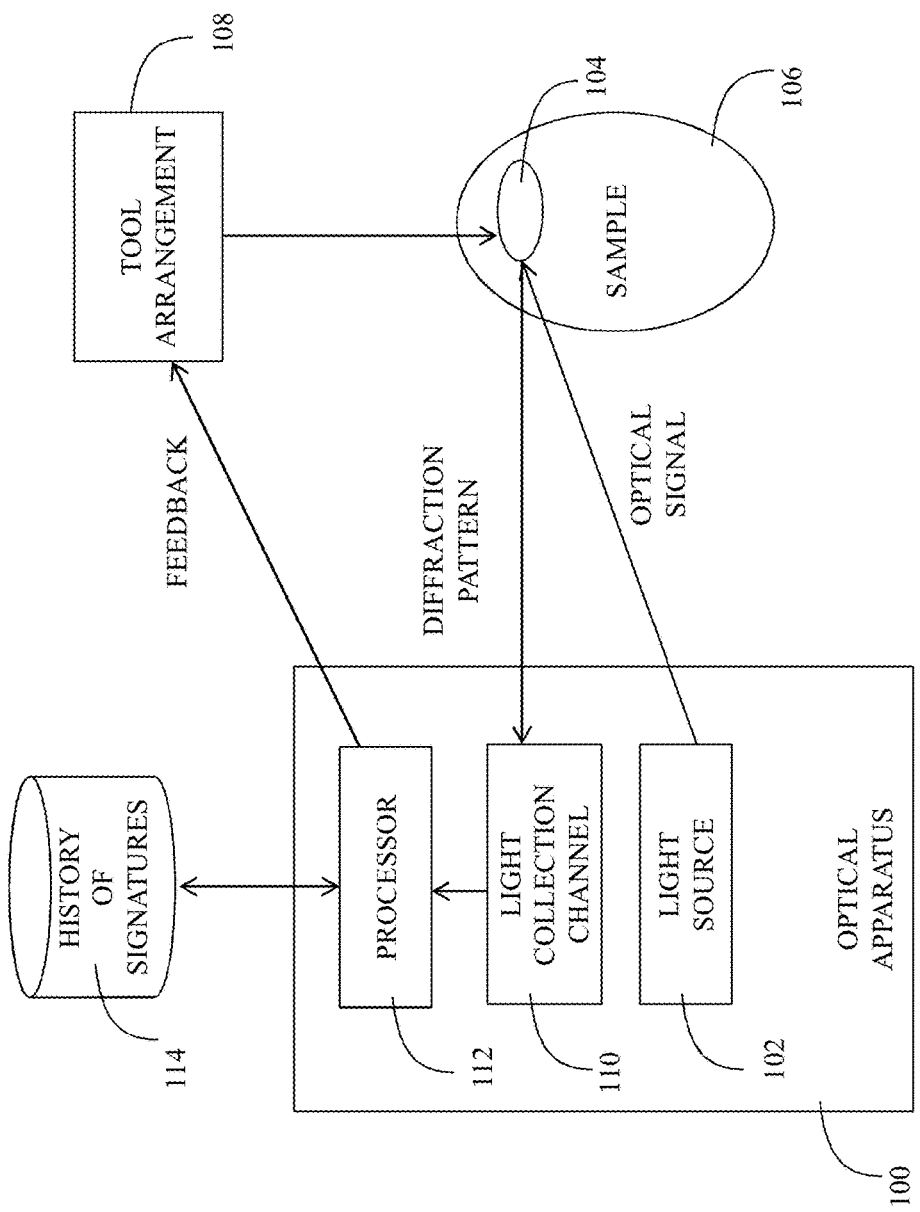
FIGS. 1A-E are simplified conceptual illustrations of a system for testing a lithographic process using a non-zero order diffraction technique, constructed and operative in accordance with an embodiment of the invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical data storage device, a magnetic data storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Reference is now made to FIG. 1A, which is a simplified conceptual illustration of a system for testing a lithographic process using a non-zero order diffraction technique, constructed and operative in accordance with an embodiment of the invention. Typical photolithographic processes produce multiple layers of structures. Light returned from such complex structures will be affected by diffracting structures of interest and also by underlying layers. However, a non-zero order diffraction signal is less sensitive to layers beneath the diffracting structure, and thus offers a benefit over zero-order diffraction, or specular reflection. In the system of FIG. 1A, optical apparatus 100 is preferably configured to obtain a non-zero order diffraction signal, and includes a light source 102 that is configured to emit an optical signal to illuminate a testing area 104 on a sample 106, such as a silicon wafer or any other material used in making integrated circuits. Testing area 104 preferably includes a periodic structure, such as may be produced on testing area 104 of target 106 by a photolithography tools arrangement 108 and formed by developed photoresist in accordance with a predefined control setting, such as an exposure dose and/or focus setting of an exposure beam emitted by photolithography tool arrangement 108. A light collection channel 110, which may include a configuration of any of collection optics, spectrometers, or detector arrays, is preferably configured to collect any non-zero diffracting order signals resulting from illuminating the periodic structure within testing area 104. Examples of a measurement system utilizing non-zero order detection channels are disclosed in U.S. Pat. No. 6,657,736, assigned to the assignee of the present application, and incorporated herein by reference with respect to the scatterometry-based optical measurement system described herein. Although the invention is exemplified hereinbelow as being associated with optical measurement system, it is appreciated that the invention is not limited to this specific application.

A processor 112 is preferably configured to process the non-zero diffracting order signals, alternatively referred to herein as a signature, collected by collection channel 110. Processor 112 preferably searches a history of reference signatures 114 to identify a reference signature that matches the test signature, such as in accordance with a predefined matching criterion and using conventional techniques, such as computer learning or expert system or neural networks technique. If a matching reference signature is found, processor 112 preferably compares the control setting associated with the test signature to a reference control setting that is associated with the matching reference signature, and the results of the comparison may be reported using conventional techniques, such as to an operator of etching apparatus 108. The results of the comparison may thus be used to determine whether or not photolithography tool arrangement 108 is operating properly. The result of the comparison may be used to provide feedback to photolithography tool arrangement 108, such as by providing the reference control setting that is associated with the matching reference signature to photolithography tool arrangement 108, which photolithography tool arrangement 108 may use to adjust its current settings. Additionally or alternatively, the result of the comparison may be reported and used to indicate whether target 106 meets predefined requirements.

The test signature may be stored in association with the predefined control setting of photolithography tool arrangement 108 for future use as a reference signature and associated reference control setting respectively in reference signatures 114.

The reference signatures in reference signatures 114 are preferably produced in the manner described above with respect to FIG. 1A using the same photolithography tool arrangement 108 as above, and using various control settings for photolithography tool arrangement 108, multiple periodic structures, such as are described in greater detail hereinbelow with respect to FIGS. 2A-G.

Figure 1B:
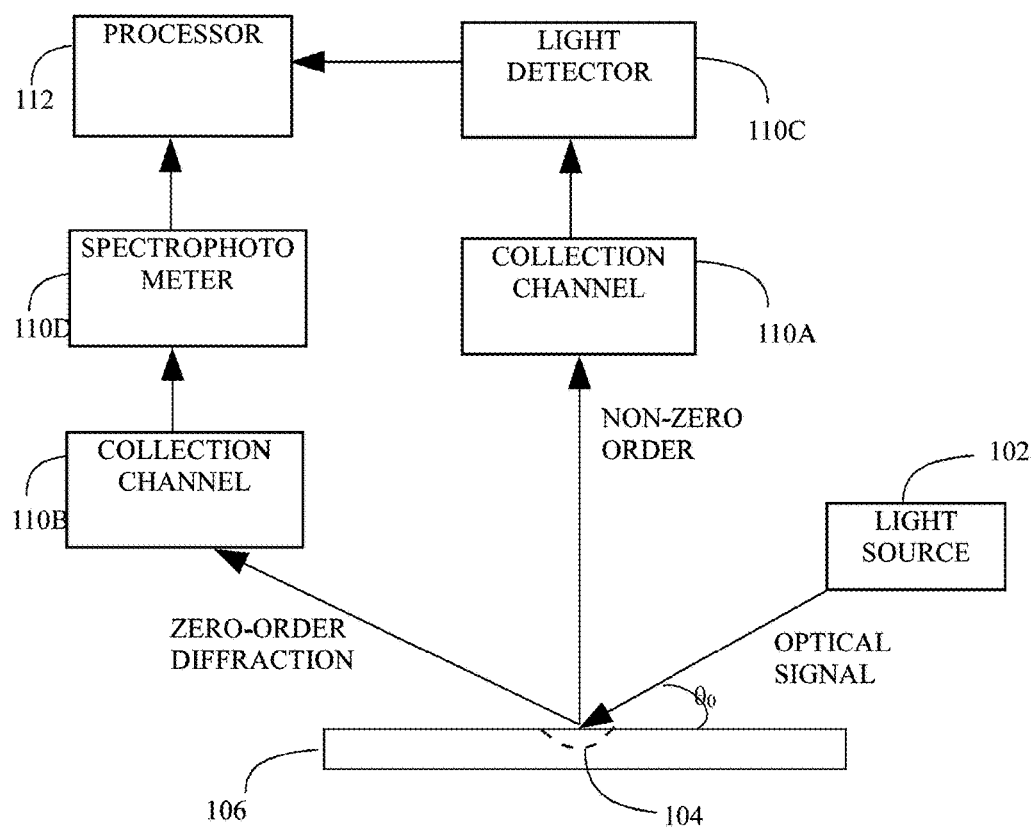

Reference is now made to FIGS. 1B-E, which are simplified conceptual illustrations of a plurality of configurations of optical apparatus 100 of FIG. 1A, constructed and operative in accordance with embodiments of the invention. Referring to FIG. 1B, light source 102 is configured to emit an optical signal to illuminate testing area 104 of target 106 at an incident angle '$\theta_0$'. The pattern of testing area 104 preferably is designed such that it diffracts part of illuminating light into non-zero (e.g., $-1^{st}$ order) signals. A collection channel 110A is preferably configured to collect such non-zero order signals, such as where it is in a normal incidence configuration to an oblique illuminating angle '$\theta_0$'. Zero-order diffracting signals (i.e., reflected) is optionally collected by a collection channel 110B and further detected by a spectrophotometer 110D.

A non-zero order measurement channel may use a light detector 110C of any appropriate type, such as a linear detector array of a plurality of photodiodes, CCD, CMOS, etc. No spectrophotometer is required. However, a spectrophotometer may optionally be used to get information on the spectral content of any non-zero order diffraction signals. The collected signal or signature is preferably processed at processor 112 as described herein. Elements 110A, 110B, 110C, and 110D are collectively represented by collection channel 110 in FIG. 1A.

Figure 1C:
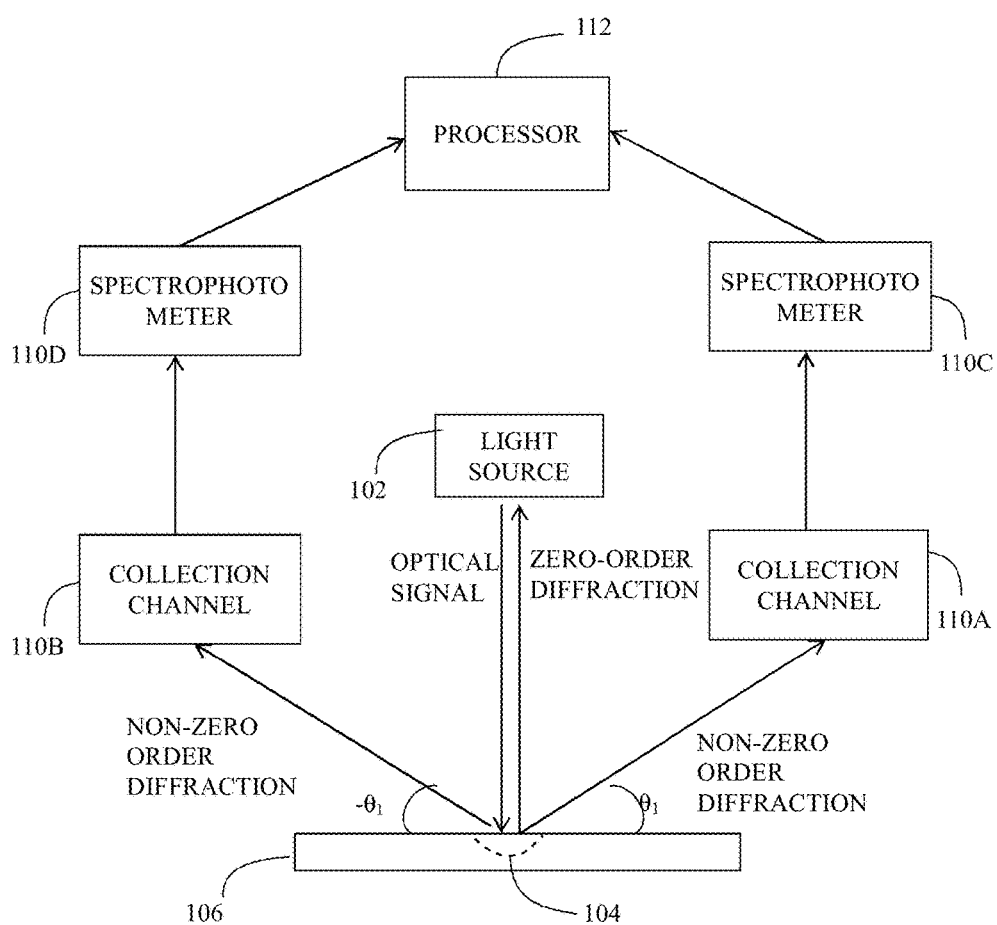

Referring to FIG. 1C, light source 102 emits an optical signal at an angle that is normal to the surface of testing area 104 of target 106. A diffracting grating within testing area 104 diffracts light into symmetric positive and negative diffraction orders at angles $+\theta_1$ and $-\theta_1$, respectively. Collection channels 110A and 110B are preferably situated on either side of light source 102 such that they are able to simultaneously collect both positive and negative order's signals. The collected diffracted light is sent to detectors 110C and 110D, respectively, and preferably processed by processor 112 as described herein. Optionally, a spectrophotometer may be used to get information on the spectral content of any non-zero order diffraction signals.

Figure 1D:
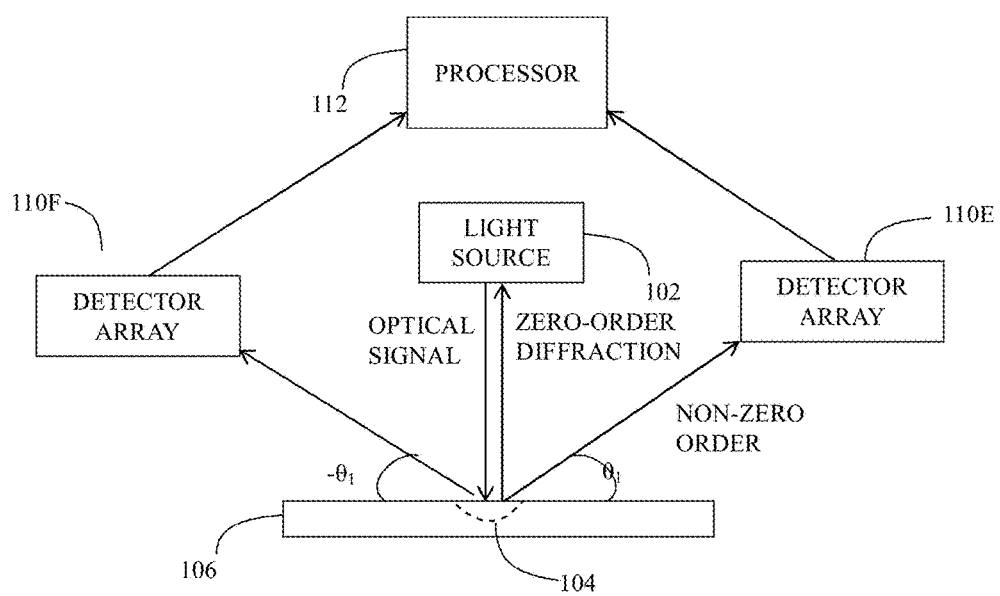
Figure 1E:
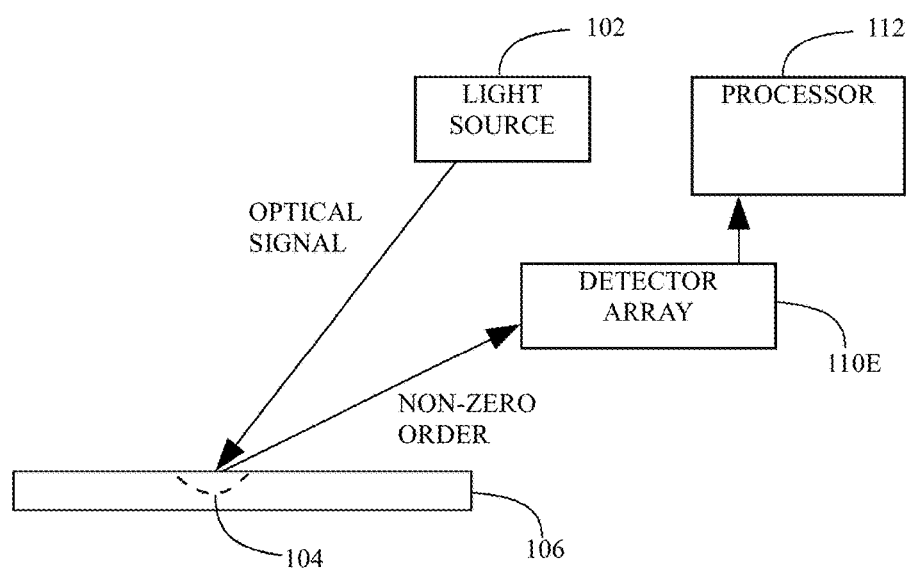

Referring to FIGS. 1D-E, collection apparatus 110 of FIG. 1A includes one or more detector arrays 110E-G Referring specifically to FIG. 1D, a similar optical arrangement to that of FIG. 1C is shown with the notable difference that detector arrays 110E and 110F are preferably situated on either side of light source 102 such that they are able to simultaneously collect both positive and negative non-zero order diffraction signals that are then processed by processor 112. Referring specifically to FIG. 1E, a non-symmetric optical configuration is shown enabling the collection of larger diffraction angles, allowing for configuring a shorter period for the periodic structure in testing area 104 of target 106.

Reference is now made to FIGS. 2A-G, which are simplified exemplary illustrations of various periodic structures that may be employed in testing area 104 of FIG. 1A, constructed and operative in accordance with embodiments of the invention. The periodic structures shown in FIGS. 2A-G are designed to produce non-symmetric, non-zero order diffraction patterns. In order to produce at least a first-order diffraction signal, the period d of a periodic structure is typically greater than the wavelength of the illuminating optical signal divided by two, or $\lambda/2$. However, for practical optical arrangements, typically $\lambda \sim d$. Thus, if the wavelength of the optical signal is in the visible spectrum, the period d is approximately 1 micron. For 1:1 duty cycle line-space dimensions of such structures are sufficiently bigger than current technology design rules and could not be used for process control due to weak correlation with focus dependent behavior of real patterned structures on the wafer. Using another duty cycle where the width of isolated lines are much smaller than the period will suffer from weak diffraction signals.

The following is a general diffraction equation that describes the dispersion of light on diffraction gratings as represented by the periodic structures described herein:

$$n^*\lambda = d^*(\sin \theta_1 - \sin \theta_0) \quad \text{(Eq. 1)}$$

where n is the order of the diffraction, $\lambda$ is the wavelength of the light, d is the period of the grating, $\sin \theta_1$ is the incident angle of the illumination beam, and $\sin \theta_0$ is the incident angle of the diffracted beam. Wavelength $\lambda$ is preferably selected in a manner to produce a non-zero order diffraction signal when an optical signal of wavelength $\lambda$ illuminates the periodic structure. FIGS. 2A-F illustrate a variety of periodic structures that are designed in accordance with Eq. 1 with a period d such that, a non-zero order diffraction signal is produced that provides useful details of the periodic structure. The periodic structures illustrated in FIGS. 2A-F preferably include a plurality of features within a period d, such as lines whose width is within a predefined range of the design rules, where either the features have substantially different widths, or the spaces between the features have substantially different widths, thus providing a high sensitivity to focus variations, such as of the exposure beam of a photolithographic arrangement, as well as creating a useful non-zero order diffraction pattern due to the long periodicity, while maintaining a sufficiently strong diffracting signal due to scattering from a significant portion of the period. Furthermore, by using asymmetric patterns within the periodic structures, the focus conditions of the exposure beam of a photolithographic arrangement could be measured as a difference, or ratio, between the resulting positive and negative orders diffraction signals, thus reducing sensitivity to factors such as diffraction or reflection from underlying layers, or other experimental errors. Period d is preferably selected to produce a +− first order diffraction signal with a relatively high wavelength $\lambda$, typically in the visual range +UV, thus enabling the production of higher order diffraction patterns, such as second and third order diffraction patterns, when using a shorter wavelength that is within the operating range of optical apparatus 100.

Figure 2A:
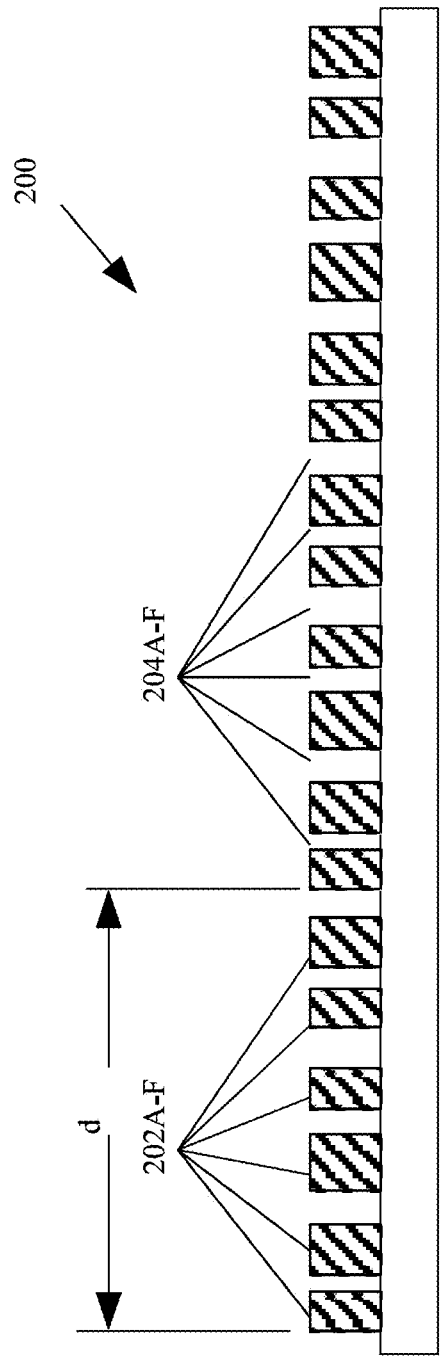

Referring to FIG. 2A, a one-dimensional periodic structure 200 is shown that is configured to produce a non-symmetric, non-zero order diffraction signals, when used in the system of FIGS. 1A-1E. Within each period d, periodic structure 200 includes alternating lines 202A-F and spaces 204, where the widths of lines 202A-F and spaces 204 vary randomly, preferably producing different intensities for diffraction orders +1 and −1.

Figure 2B:
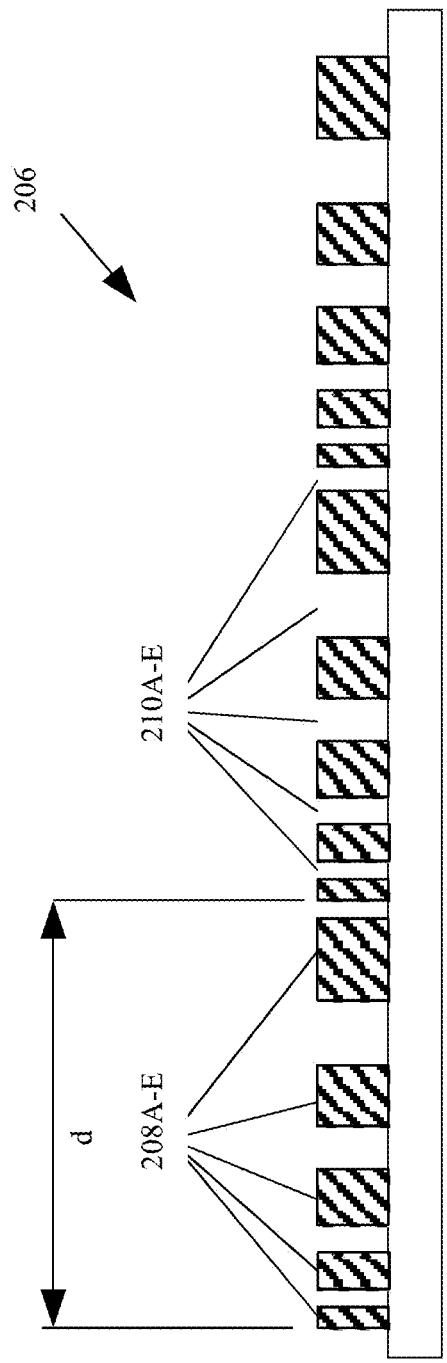

Referring to FIG. 2B, another one-dimensional periodic structure 206 is shown that is configured to produce a non-symmetric, non-zero order diffraction signals, when used in the system of FIG. 1A. Within each period d, periodic structure 206 includes a plurality of alternating lines 208 and spaces 210, where both the widths of lines 208 and spaces 210 are monotonically increasing, thus producing different intensities for diffraction orders +1 and −1.

Referring to FIG. 2C, another one-dimensional periodic structure 212 is shown that is configured to produce a non-symmetric, non-zero order diffraction signals, when used in the system of FIG. 1A. Within each period d, periodic structure 212 includes a plurality of alternating lines 214A-F and spaces 216A-F, where the width of lines 214A-F is constant, and the widths of spaces 216A-F are monotonically increasing, thus producing different intensities for diffraction orders +1 and −1.

Figure 2D:
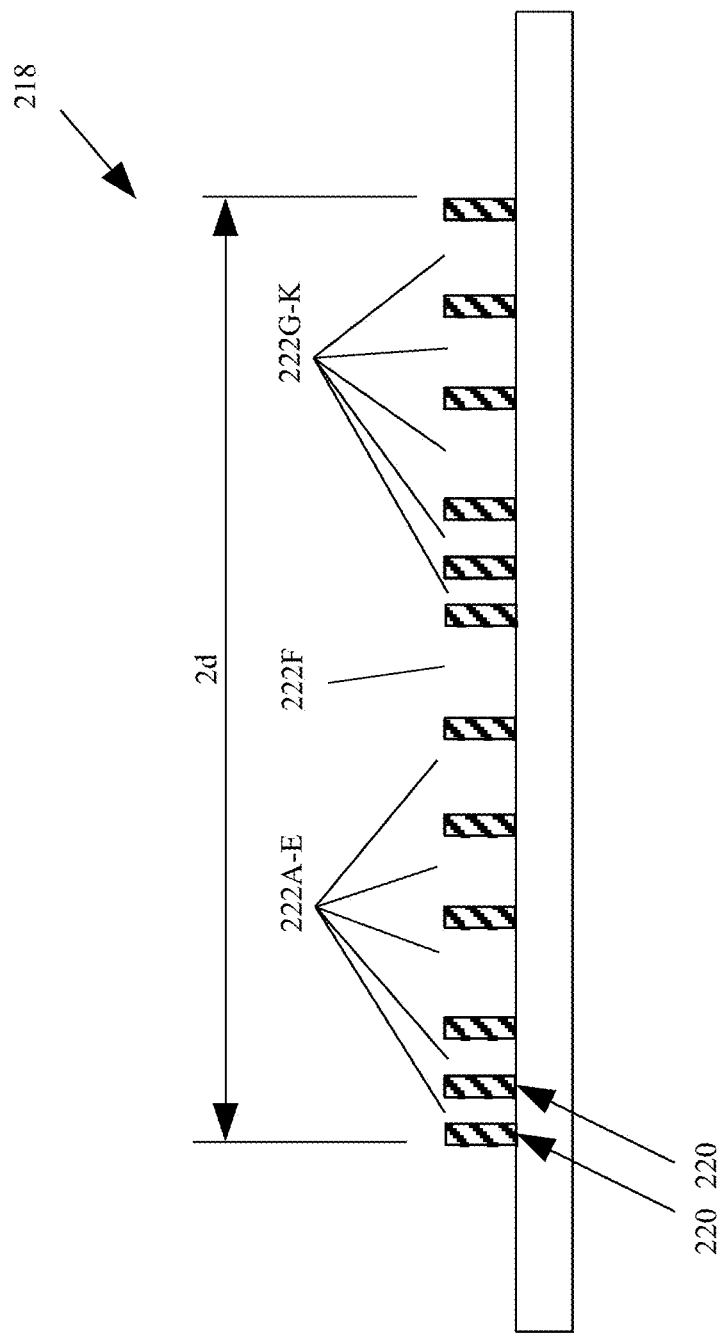

Referring to FIG. 2D, another one-dimensional periodic structure 212 is shown that is configured to produce a non-symmetric, non-zero order diffraction pattern when used in the system of FIG. 1A. The structure of FIG. 2D is similar to that of FIG. 2C with the notable difference that the periodic pattern of FIG. 2C is arranged in pairs, back to back, such that every period forms a symmetric structure having double the original period d, thus removing an error that would result from rotating target 106, which will be described below with respect to FIG. 3C. For example, lines 220 have dimensions similar to lines 214 of FIG. 2C, the widths of spaces 222A-E are similar to the widths of spaces 216A-E of FIG. 2C, and the widths of spaces 222G-K are in a reverse sequence to the widths of spaces of 216A-E. It may be noted that any of the periodic structures described in FIGS. 2A-C, and 2F-G are configurable according to the geometry of periodic structure 218.

Figure 2E:
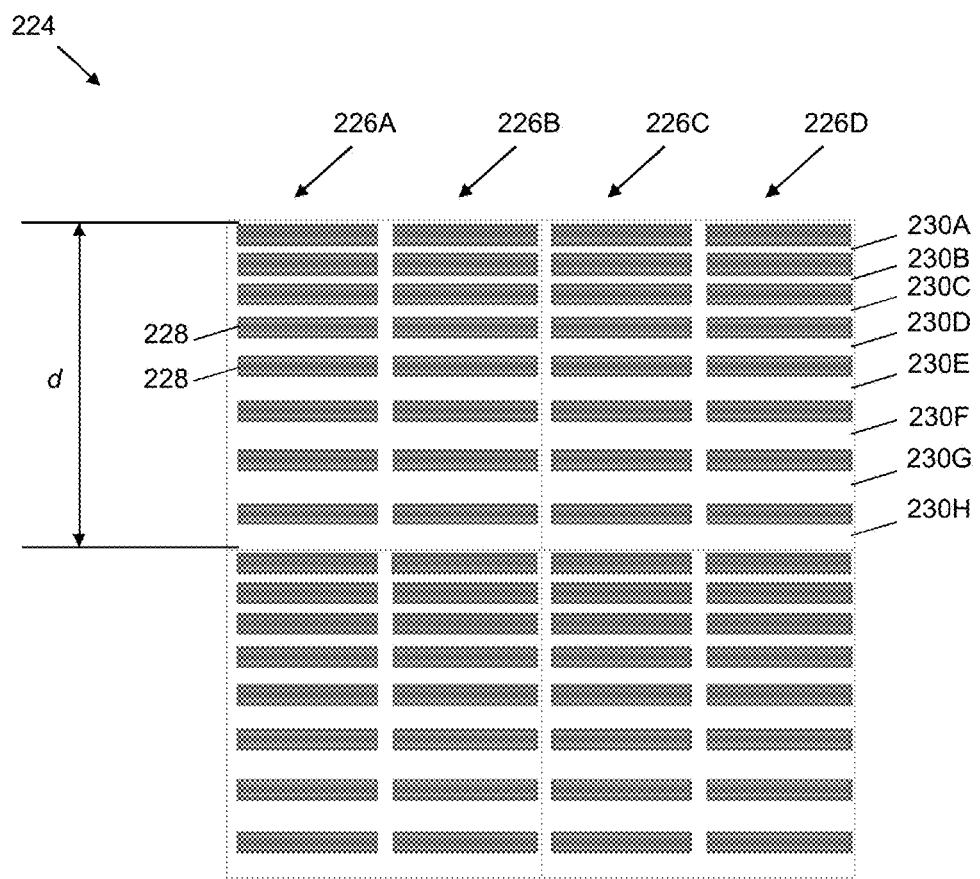

Referring to FIG. 2E, a two-dimensional periodic structure 224 is shown that is configured to produce a non-symmetric, non-zero order diffraction pattern, when used in the system of FIG. 1A. Structure 224 is designed to produce a diffraction effect similar to 'blazing' that is typically achieved with a three-dimensional saw-tooth periodic structure. Each period d of structure 224, includes a plurality of identical sets 226A-D of alternating lines 228 and spaces 230A-G, where the width of lines 228 is constant and the widths of spaces 230A-G is monotonically increasing.

Figure 2F:
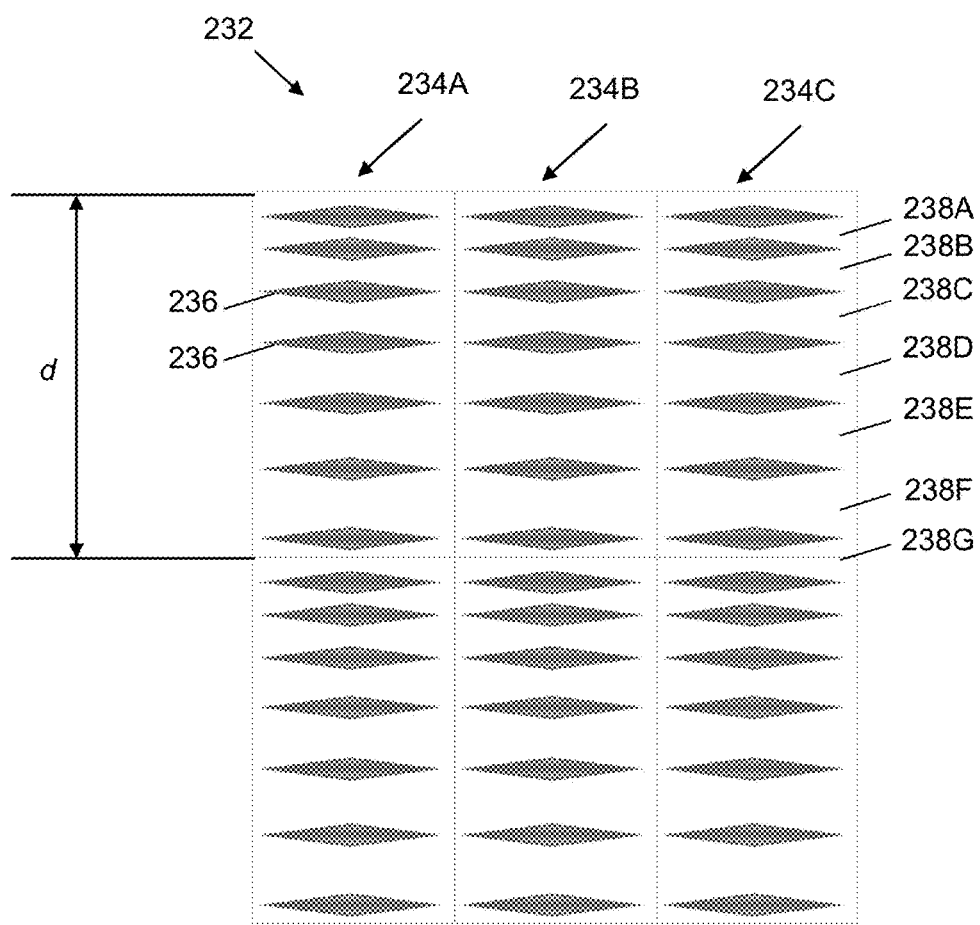

Referring to FIG. 2F, another two-dimensional periodic structure 232 is shown that is configured to produce a non-symmetric, non-zero order diffraction pattern, when used in the system of FIG. 1A. Each period d of structure 232 includes a plurality of identical sets 234A-C of alternating lines 236 and spaces 238A-G. Lines 236 of periodic structure 232 are similar to lines 228 of structure 224 in that lines 236 are identical to each other. However, whereas lines 228 have uniform thickness over the length of the lines, the thickness of lines 236 varies over the length of the lines. The widths of spaces 238A-G between lines 236 increase monotonically, in a manner similar to structure 224 of FIG. 2E. For example, the width of lines 236 reaches a maximum width at the middle point, and monotonically decreases, tapering to a point at the ends, thus resulting in a diamond-like shape.

Figure 2G:
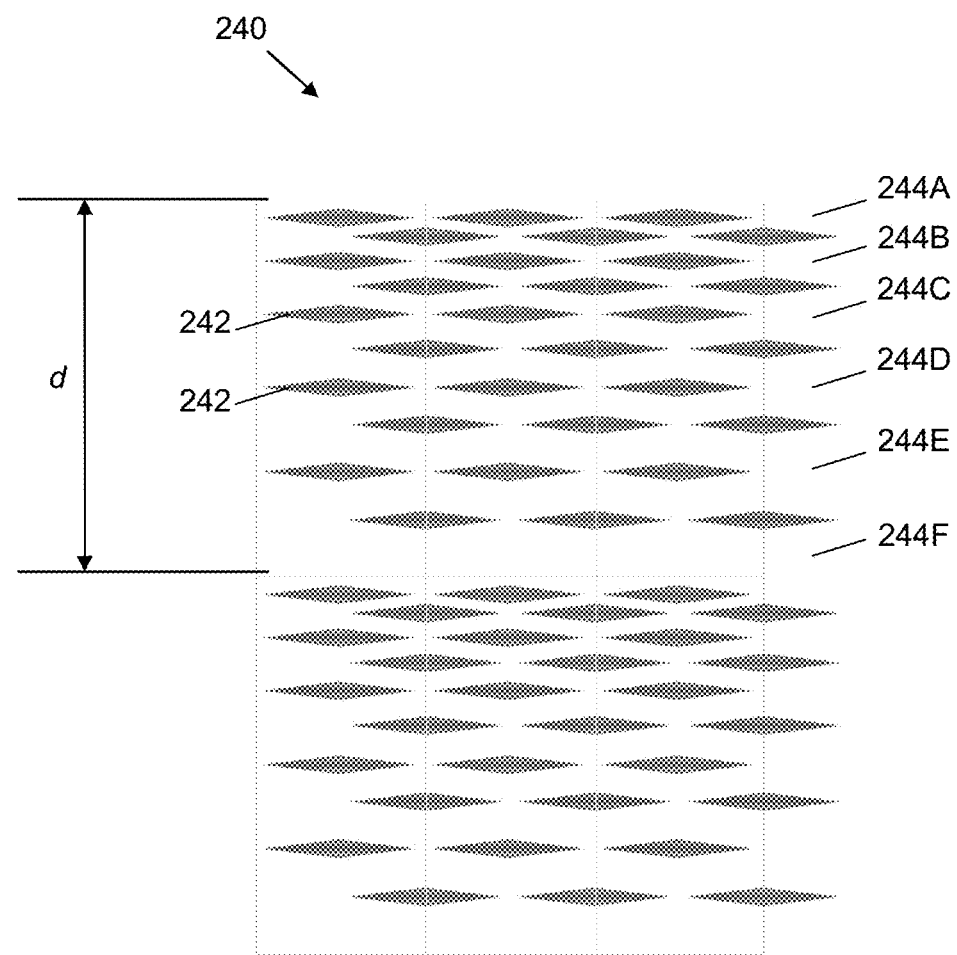

Referring to FIG. 2G, another two-dimensional periodic structure 240 is shown that is configured to produce a non-symmetric, non-zero order diffraction pattern, when used in the system of FIG. 1A. Periodic structure 240 preferably includes features 242 of uniform size and spaces 244A-F that are monotonically increasing, where features 242 preferably have a high sensitivity to focus variations, such as having sharp edges or corners, or are printed using non-printing assist features.

Other techniques for maintaining high sensitivity to focus variations include configuring the periodic structure with an assist feature with the same phase as the main feature, or by including an area in the periodic structure with a low intensity gradient that is more susceptible to focus changes.

Figure 3A:
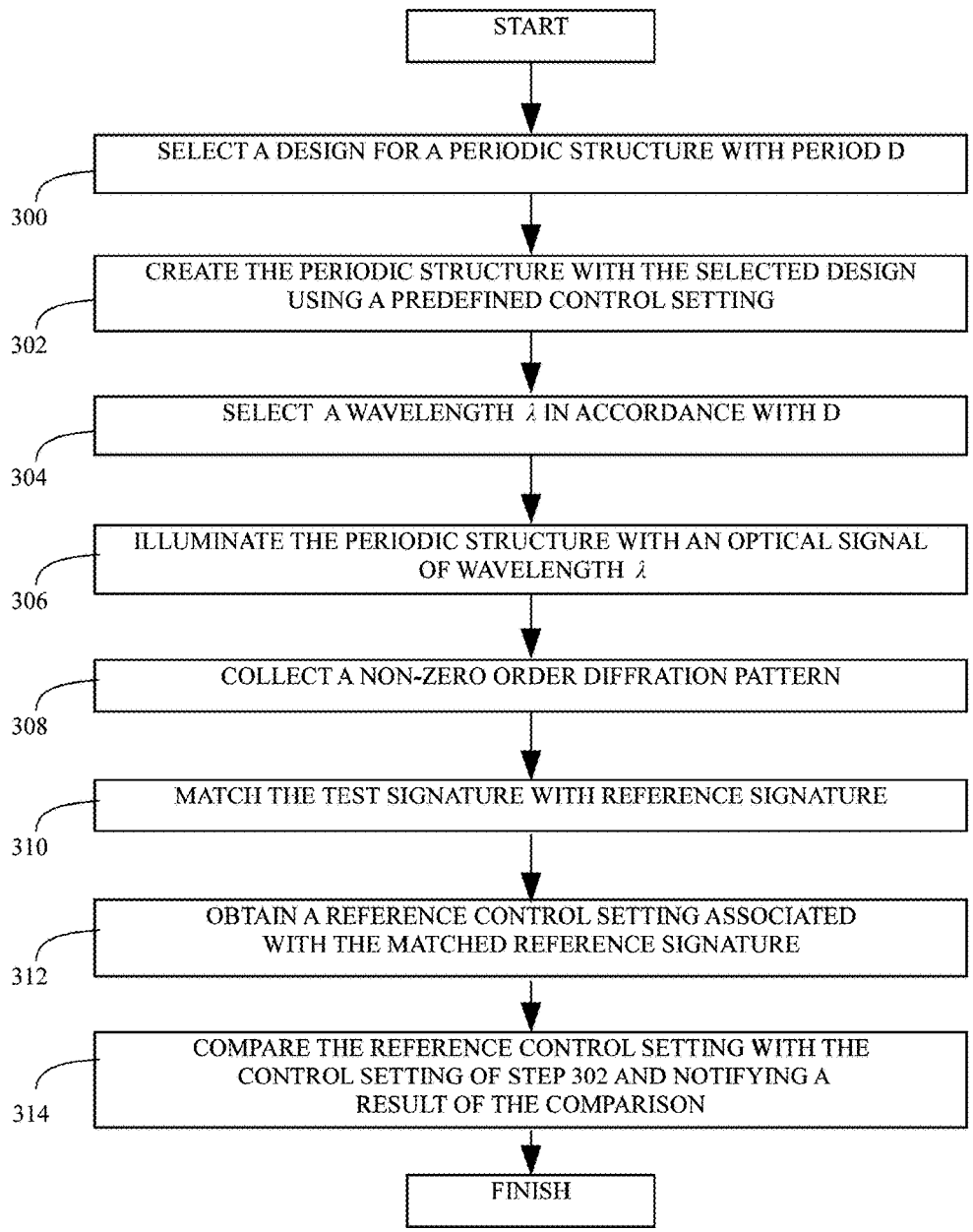
FIGS. 3A-C are simplified flowchart illustrations of an exemplary method of operation of the system of FIGS. 1A-E and 2A-G, operative in accordance with an embodiment of the invention.

Reference is now made to FIG. 3A which is a simplified flowchart illustration of an exemplary method of operation of any of the system configurations described herein, operative in accordance with an embodiment of the invention. In the method of FIG. 3A, a design for a periodic structure with period d is selected (step 300). The selected periodic structure is created within a testing area of a sample (e.g., wafer), such as by employing a lithographic process using a predefined control setting (step 302). A wavelength λ is selected or defined such that a non-zero order diffraction signal is produced when light of wavelength λ illuminates the periodic structure (step 304). Light of wavelength A illuminates the periodic structure (step 306). The resulting non-zero diffraction signal, or signature, is collected (step 308). The obtained signature is matched with a reference signature (step 310). A reference control setting associated with the matched reference signature is obtained (step 312). The obtained reference control setting is compared with the predefined control setting of step 302 (step 314).

Figure 3B:
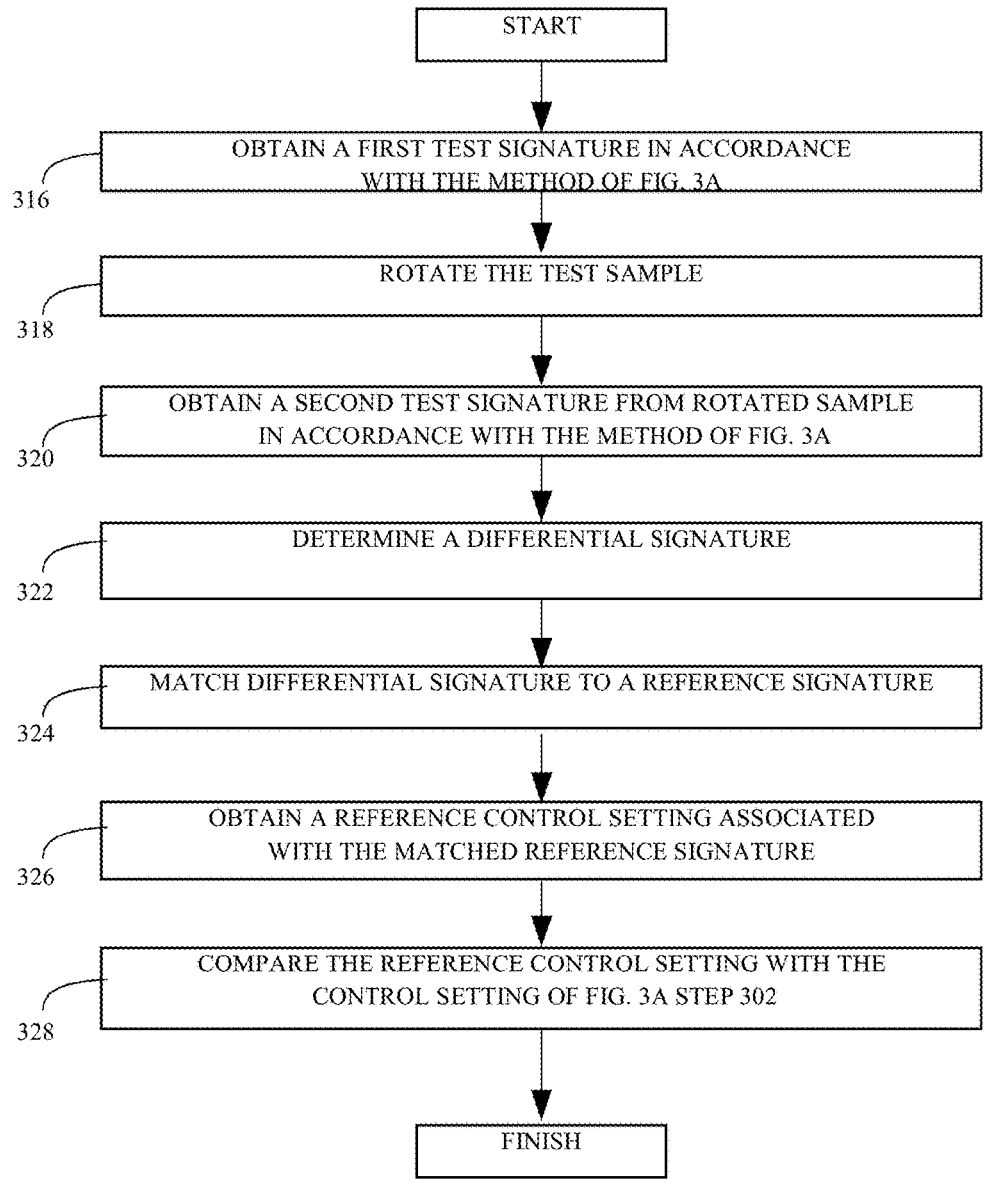

Reference is now made to FIG. 3B which is a simplified flowchart illustration of an exemplary method of operation of the system of FIG. 1A, operative in accordance with another embodiment of the invention. In the method of FIG. 3B, a first signature is obtained from a testing area of a target in accordance with the method described in FIG. 3A, steps 300-308 (step 316). The test sample is preferably rotated (step 318), such as by rotating the test sample by 180°, where the light source and/or the collection optics are preferably symmetric to the rotation of the test sample, such as by being situated normal to the test sample. A second signature is obtained from the rotated sample in accordance with the method described in FIG. 3A, steps 304-310 (step 320) using the same wavelength λ that was used to obtain the first signature. A differential signature is determined (step 322), such as by subtracting one signature from another, or by calculating a ratio of the two signatures and matched to a reference signature (step 324). A reference control setting associated with the matched reference signature is obtained (step 326). The reference control setting is compared with the control setting of FIG. 3A, step 302 (step 328). Instead of test sample rotation, the orientation (i.e., azimuth) of the light source and/or the collection optics relative to the test sample may be alternated.

Figure 3C:
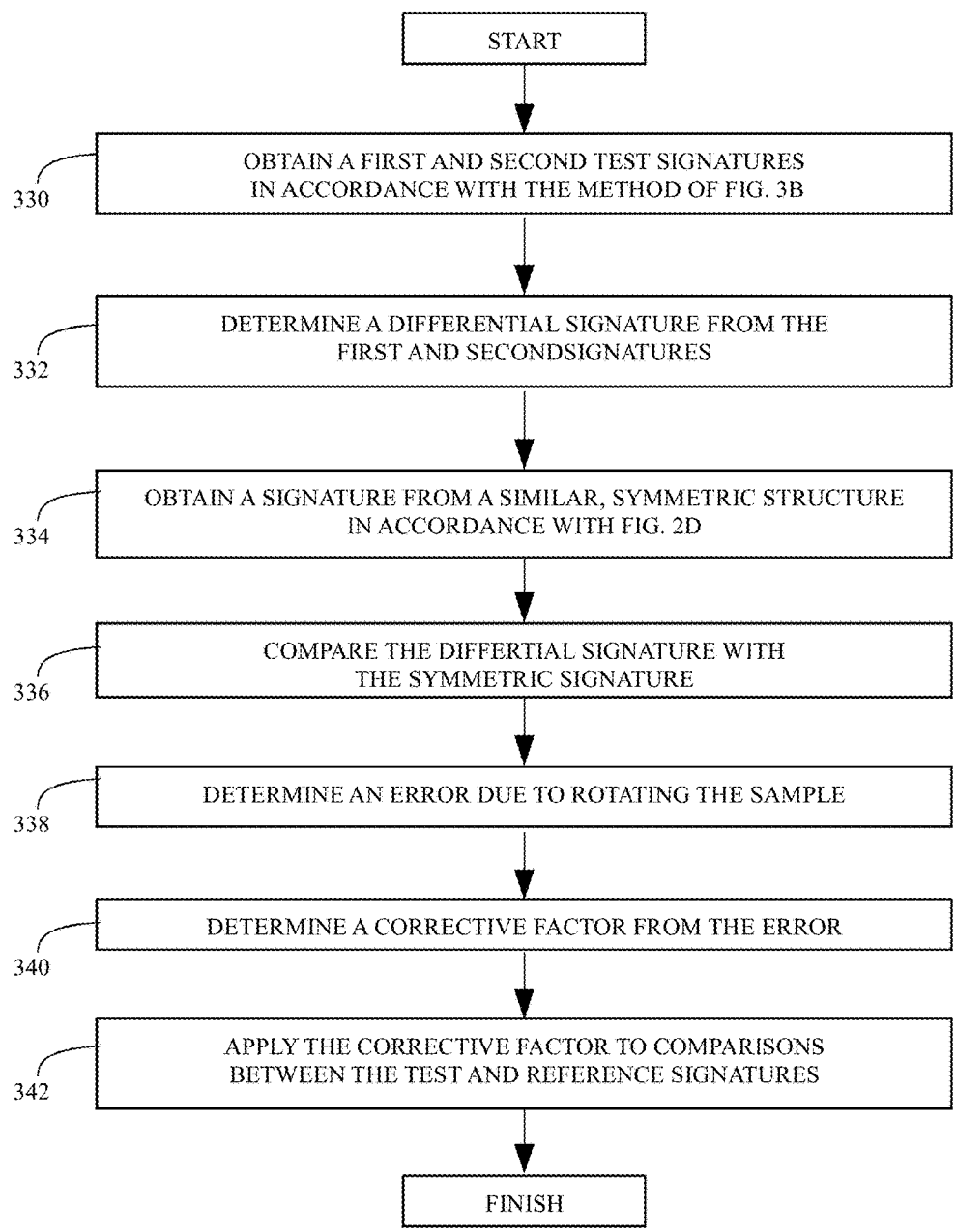

Reference is now made to FIG. 3C which is a simplified flowchart illustration of an exemplary method of operation of the system of FIG. 1A, operative in accordance with an embodiment of the invention. The method of FIG. 3C is substantially similar to that of FIG. 3B with the notable difference that upon obtaining first and second test signatures in accordance with the method of FIG. 3B (step 330), and determining a differential signature of the first and second test signatures (step 332), a signature of a symmetric periodic structure is obtained (step 334), such as of the periodic structure that is described in FIG. 2D. The differential signature is compared with the symmetric signature (step 336), and an error due to rotating the sample is determined (step 338). A corrective factor is determined from the error (step 340) and the corrective factor is applied to further comparisons between the test and reference signatures (step 342).

The flowchart and block diagrams in the Figures illustrate the architecture, functionality, and operation of possible implementations of systems, methods and computer program products according to various embodiments of the invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It will be appreciated that any of the elements described hereinabove may be implemented as a computer program product embodied in a computer-readable medium, such as in the form of computer program instructions stored on magnetic or optical storage media or embedded within computer hardware, and may be executed by or otherwise accessible to a computer (not shown).

While the methods and apparatus herein may or may not have been described with reference to specific computer hardware or software, it is appreciated that the methods and apparatus described herein may be readily implemented in computer hardware or software using conventional techniques.

While the invention has been described with reference to one or more specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention. For example, the invention may be adapted for use with other types of pattern creation manufacturing steps, such as with etching.

The invention claimed is:

1. A method of controlling a manufacturing process, the method comprising the steps of:
  a) providing a testing area with a periodic structure having a period d, wherein within each period d the periodic structure includes a plurality of alternating lines and spaces therebetween, and wherein said lines and spaces within said each period d have a monotonically increasing width;

b) illuminating the periodic structure with a light, thereby producing a plurality of non-zero order diffraction signals;

c) collecting the diffraction signals to produce a test signature;

d) matching the test signature with a reference signature; and e) controlling a manufacturing process using a control setting set associated with the matching reference signature.

2. The method according to claim 1, wherein the manufacturing process is a lithography process, and wherein the control setting set includes any of exposure energy and focus conditions of exposing light.

3. The method according to claim 1, wherein the periodic structure is present on a semiconductor wafer.

4. The method according to claim 1, wherein any of steps a), b), c), d) and e) are performed to control a lithography process applied to structures progressing on a production line.

5. The method according to claim 1 and further comprising selecting a wavelength of said light, wherein the non-zero order diffraction signal is produced when the light of the selected wavelength illuminates the periodic structure.

6. The method according to claim 1 wherein the illuminating is performed at a first angle with respect to the periodic structure, wherein the collecting is performed at a second angle with respect to the periodic structure, and wherein the illuminating and the collecting are performed at different points in space.

7. The method according to claim 1, wherein the reference signature was previously produced by performing steps a), b), and c) with respect to a reference structure.

8. The method according to claim 1 wherein said plurality of non-zero order diffraction signals includes positive and negative diffraction orders and the test signature includes a differential signal obtained from corresponding positive and negative diffraction orders.

9. The method according to claim 1 wherein the providing comprises providing the periodic structure having a period d that is greater than a wavelength A of the light divided by two.

10. The method according to claim 1, wherein the illuminating comprises selecting a wavelength $\lambda$ of the light, and wherein $\lambda \sim d$.

11. The method according to claim 1, wherein the reference signature was previously produced by using a theoretical model.

12. The method according to claim 1, wherein said positive (+) and negative (−) diffraction orders includes +1 and −1 diffraction orders.

13. The method according to claim 1, wherein said positive (+) and negative (−) diffraction orders includes higher diffraction orders.

* * * * *